United States Patent [19]

Comins

[11] Patent Number: 5,428,166
[45] Date of Patent: Jun. 27, 1995

[54] METHOD OF MAKING ASYMMETRIC DE RING INTERMEDIATES FOR THE SYNTHESIS OF CAMPTOTHECIN AND CAMPTOTHECIN ANALOGS

[75] Inventor: Daniel L. Comins, Cary, N.C.

[73] Assignee: North Carolina State University, Raleigh, N.C.

[21] Appl. No.: 226,877

[22] Filed: Apr. 12, 1994

Related U.S. Application Data

[63] Continuation-in-part of Ser. No. 41,782, Apr. 1, 1993, Pat. No. 5,315,007, which is a continuation-in-part of Ser. No. 900,650, Jun. 18, 1992, Pat. No. 5,212,317.

[51] Int. Cl.$^6$ .............. C07D 491/048; C07D 491/052
[52] U.S. Cl. ....................................... 546/116; 546/48
[58] Field of Search ......................................... 546/116

[56] References Cited

U.S. PATENT DOCUMENTS

| | | | |
|---|---|---|---|
| 4,578,381 | 3/1986 | Uchida et al. | 514/233 |
| 4,894,456 | 1/1990 | Wall et al. | 546/41 |
| 5,162,532 | 11/1992 | Comins et al. | 546/48 |
| 5,191,082 | 3/1993 | Comins et al. | 546/116 |
| 5,212,317 | 5/1993 | Comins et al. | 546/301 |
| 5,243,050 | 9/1993 | Comins et al. | 546/116 |
| 5,342,947 | 8/1994 | Lackey et al. | 546/41 |

FOREIGN PATENT DOCUMENTS 0325247  7/1989  European Pat. Off. .

OTHER PUBLICATIONS

Comins, D. L., et al., Lithiation of Methoxypyridines Directed by α-Amino Alkoxides, *The Journal of Organic Chemistry*, 55:69 (1989).

Comins, D. L., et al., Ortho Lithiation of 2-, 3-, and 4-Methoxypyridines, *Tetrahedron Letters*, 29:773-776 (1988).

Lyle, R. E., et al., Synthetic Approaches to Camptothecin, Abstracts, *23rd International Congress of Pure and Applied Chemistry*, Abstracts, p:67 (1971).

Lyle, R. E., et al., "The Synthesis of an Analog of Camptothecin by a General Method", *The Journal of Organic Chemistry*, 38:3268-3271 (1973).

Comins, D. L., et al., Ortho Metalation Directed by α-Amino Alkoxides, *the Journal of Organic Chemistry*, 49:1078-1083 (1984).

Comins, D. L., et al., "Ortho Substitution of m-Anisaldehyde via α-Amino Alkoxide Directed Lithiation", *The Journal of Organic Chemistry*, 54:3730-3732 (1989).

Bristol, J. A., et al., Analogs of Camptothecin, *The Journal of Medicinal Chemistry*, 18:535 (1975).

Abramovitch, Pyridine and Its Derivatives, *Heterocyclic Compounds*, Suppl. Pt. 3., 14:745-753 (1974).

Sugasawa, T., et al., "Experiments on the Synthesis of dl-Camptothecin. II.—Synthesis of a D-E Ring Analog of Camptothecin and a Total Synthesis of Ricinine", *Chem. Pharm. Bull.*, 22:763-770 (1974).

Plattner, J. J., et al., Synthesis of Some DE and CDE Ring Analogs of Camptothecin, *The Journal Of The American Chemical Society*, 94:24:8613-8615 (1972).

Cai, J. Camptothecin, *The Alkaloids*, 21:101-137 (1983).

Comins, D. L., A 10-Step Asymmetric Synthesis of (S)-Camptothecin, *Journal of the American Chemical Society*, pp. 10971-10972 (1992).

Comins, D. L., Ph.D. Thesis, University of New Hampshire, Durham, New Hampshire pp. 25-29 (1977).

*Primary Examiner*—Bernard Dentz
*Attorney, Agent, or Firm*—Bell, Seltzer, Park & Gibson

[57]  ABSTRACT

A method of making racemic DE ring intermediates for the synthesis of camptothecin and camptothecin analogs employing novel intermediates of Formula XX and XXI:

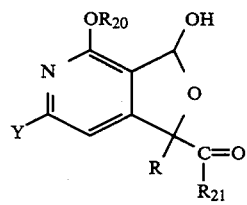

XX (Abstract continued on next page.)

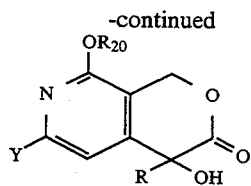

XXI as precursors to the DE ring intermediate.

The present invention also provides camptothecin analog of Formula I-A

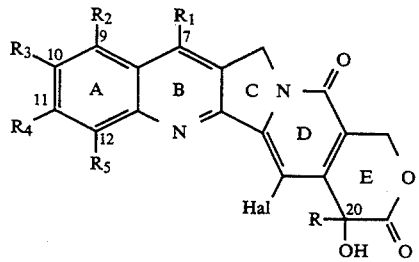

(I-A)

wherein:
Hal is a halogen is selected from the group consisting of F, Cl, and Br;
R may be loweralkyl;
$R_1$ may be H, loweralkyl, loweralkoxy, or halo;
$R_2$, $R_3$, $R_4$, and $R_5$ may each independently be H, amino, hydroxy, loweralkyl, loweralkoxy, loweralkyl-thio, di(loweralkyl)amino, cyano, methylenedioxy, formyl, nitro, halo, trifluoromethyl, amninomethyl, azido, amido, hydrazino, or any of the twenty standard amino acids bonded to the A ring via the amino-nitrogen atom.

Additionally, novel compounds useful in the preparation of the compounds of Formula I-A are also provided.

26 Claims, No Drawings

METHOD OF MAKING ASYMMETRIC DE RING INTERMEDIATES FOR THE SYNTHESIS OF CAMPTOTHECIN AND CAMPTOTHECIN ANALOGS

RELATED APPLICATIONS

This application is a continuation-in-part of U.S. patent application Ser. No. 08/041,782, filed 1Apr. 1993, now U.S. Pat. No. 5,315,007, which is a a continuation-in-part of U.S. patent application Ser. No. 07/900,650, filed 18 Jun. 1992, now U.S. Pat. No. 5,212,317, the disclosures of which are incorporated herein by reference in their entirety.

FIELD OF THE INVENTION

The present invention provides a method of making racemic DE ring intermediates useful for the synthesis of camptothecin and camptothecin analogs.

BACKGROUND OF THE INVENTION

Camptothecin (Chem. Abstracts Registry No. 7689-03-4) is a naturally occurring compound found in *Camptotheca acuminata* (Nyssaceae) which has antileukemic and antitumor properties. Numerous camptothecin analogs having like properties are known, examples being those described in U.S. Pat. No. 4,894,456 to Wall et al. and European Patent Application No. 0 325 247 of Yaegashi et al.

A number of syntheses for camptothecin and camptothecin analogs are known. Most recently, parallel synthesis for camptothecin and camptothecin analogs have been disclosed in U.S. Pat. No. 5,162,532 to Comins and Baevsky. According to the methods disclosed therein, camptothecin and analogs thereof are prepared from the intermediates disclosed therein. One of the intermediates disclosed therein is the DE ring intermediate.

One method of synthesizing the DE ring intermediate was previously disclosed Comins, D. L. The Synthesis of Analogs of Camptothecin, *Ph.D. Thesis, University of New Hampshire*, May 1977. A second method was disclosed in U.S. Pat. No. 5,162,532 to Comins and Baevsky. Subsequently, U.S. Pat. No. 5,212,317 to Comins and Baevsky, disclosed an alternate method of producing the DE ring intermediate.

An object of the present invention is to provide new methods for preparing compounds of Formula III above and novel intermediates useful for the preparation of such compounds, all of which are useful for the synthesis of camptothecin and camptothecin analogs.

SUMMARY OF THE INVENTION

The present invention provides a method of making compounds of Formula XX and XXI:

(XX)

(XXI)

wherein $R_{20}$ is loweralkyl, $R_{21}$ is lower alkoxy, R is loweralkyl, and Y is H or halogen.

These compounds are useful in the preparation of compounds of Formula III, (III)

wherein R is loweralkyl and Y is H or halogen, which in turn is useful in the production of compounds of Formula I:

(I)

wherein:

R may be loweralkyl, $R_1$ may be H, loweralkyl, loweralkoxy, or halo, $R_2$, $R_3$, $R_4$, and $R_5$ may each independently be H, amino, hydroxy, loweralkyl, loweralkoxy, loweralkylthio, di(loweralkyl)amino, cyano, methylenedioxy, Formyl, nitro, halo, trifluoromethyl, amninomethyl, azido, amido, hydrazino, or any of the twenty standard amino acids bonded to the A ring via- the amino-nitrogen atom (numbering in Formula I is by the Le Men-Taylor numbering system and rings are lettered in the conventional manner. See U.S. Pat. No. 5,162,532 to Comins and Bearsky.

In one embodiment illustrated by Scheme D,

Scheme D

XX → XXI

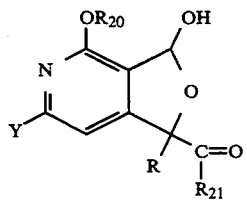

-continued
Scheme D

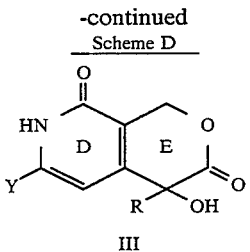

III racemic compounds of Formula III are produced.

The present invention also provides camptothecin analog of Formula I-A

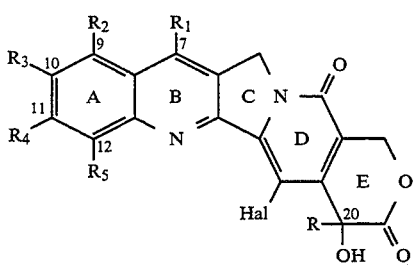

(I-A)

wherein Hal is a halogen, preferably selected from the group consisting of F, Cl, Br, and I, and R, $R_1$, $R_2$, $R_3$, $R_4$, and $R_5$ are as defined above for compounds of Formula I.

The compounds of Formula I-A are prepared from the novel intermediate compounds of the present invention, of Formula III-B:

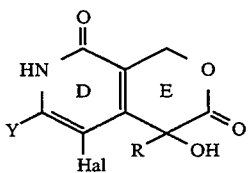

(III-B)

wherein Hal is a halogen, preferably selected from the group consisting of F, Cl, Br, and I, and R and Y are as defined above for compounds of Formula III.

In one embodiment illustrated by Scheme E,

Scheme E

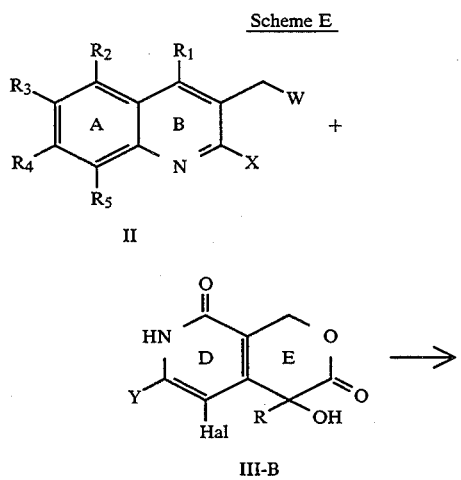

-continued
Scheme E

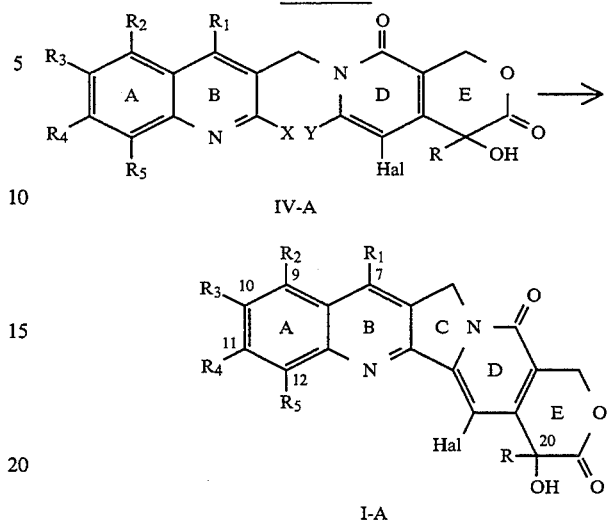

compounds of Formula I-A are produced.

DETAILED DESCRIPTION OF THE INVENTION

As used herein, the term "loweralkyl" means a linear or branched alkyl group with 1–8, preferably 1–4, carbon atoms, such as methyl, ethyl, propyl, isopropyl, n-butyl, tert-butyl, hexyl, and octyl. This definition also applies to a loweralkyl moiety in the loweralkoxy, loweralkylthio, and di(loweralkyl)amino groups. Thus, examples of loweralkoxy groups are methoxy, ethoxy, propoxy, sec-butoxy, and isohexoxy; examples of loweralkylthio groups are methylthio, ethylthio, tert-butylthio, and hexylthio; and examples of di(loweralkyl)amino groups are dimethylamino, diethylamino, diisopropylamino, di(n-butyl)amino, and dipentylamino.

The terms "halo" and "halogen" as used herein refers to a substituent which may be fluoro, chloro, bromo, or iodo.

The compounds of Formula III above are, as noted above, prepared according to Scheme D below,

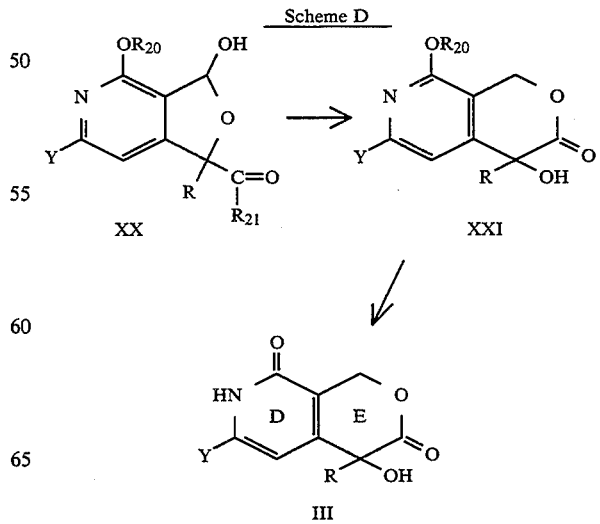

wherein R$_{20}$ is loweralkyl, R$_{21}$ is lower alkoxy, R is loweralkyl, and Y is H or halogen.

Scheme D begins with the preparation of compounds of Formula XX:

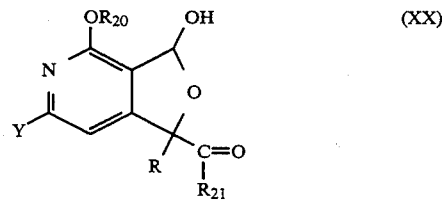

wherein:
R$_{20}$ is loweralkyl, preferrably methyl.
R$_{21}$ is lower alkoxy, preferrably methoxy.
R is loweralkyl, preferrably ethyl.
Y is H or halogen (e.g., chloro). Preferably Y is H.

The compounds of Formula XX are prepared by reacting an appropriate pyridine or substituted pyridine compound with mesityllithium, a formamide of ethylenediamine, and a base of the Formula A$^+$B$^-$, wherein A$^+$ is an inorganic cation, and B$^-$ is an organic anion.

The pyridine compound is preferably selected from the group consisting of 2-methoxypyridine and 5-chloro-2-methoxypyridine. The pyridine compound is initially reacted with mesityllithium. Mesityllithium may be prepared by reacting 2-bromomesitylene with t-butyllithium. The reaction of the pyridine with mesityllithium may be carried out in a suitable aprotic solvent such as tetrahydrofuran, ether or dimethoxyether, at variable temperatures ranging from about −75° C. to about 37° C. over the course of the reaction. The resulting mixture is then reacted with a formamide of an ethylenediamine at a temperature of between about −75° C. to 0° C. Suitable formamides of ethylenediamine include N-formyl-N,N′,N′-trimethylethylenediamine and N-formyl-N,N′,N′-triethylethylenediamine. The base of the Formula A$^+$B$^-$ is added at about −23° C., to form an intermediate.

The base A$^+$B$^-$ is a combination of an inorganic cation and an organic anion. Exemplary inorganic cations include sodium, potassium, and lithium, with lithium being more preferred. Exemplary organic anions include propyl, n-butyl, t-butyl, phenyl, and n-pentyl, with n-butyl being preferred.

The intermediate formed is then reacted with anhydrous cerium trichloride. Anhydrous cerium trichloride can be prepared by reacting hydrated cerium trichloride with a drying agent such as t-butyllithium. The anhydrous cerium trichloride is typically provided as a slurry in an aprotic solvent. Suitable aprotic solvents include tetrahydrofuran, ether and dimethoxyether, with tetrahydrofuran being preferred. The intermediate is typically reacted with anhydrous cerium trichloride at about −23° C.

The resulting mixture is further reacted with an alkyl α-ketobutyrate to produce the compound of Formula XX. Exemplary alkyl α-ketobutyrates include methyl α-ketobutyrate, ethyl α-ketobutyrate, and t-butyl α-ketobutyrate, with methyl α-ketobutyrate being preferred. The reaction is typically carried out under variable temperatures ranging from about −75° C. to −23° C. The alkyl α-ketobutyrate is preferably added to the reaction solution rapidly, in a single aliquot. The compound produced is crystalline. Purification of the resulting compound of Formula XX can be accomplished by conventional methods known to those skilled in the art. A preferred method of purification is by radial PLC.

The compound of Formula XX is then reacted with a reducing agent in a polar solvent with heat, to yield the compound of Formula XXI. Suitable reducing agents include aluminum isopropoxide, sodium borohydride, diisobutyl aluminum hydride, and sodium cyanoborohydride. Preferably the reducing agent is aluminum isopropoxide. Polar solvents include alkanols, with isopropanol being preferred. The reaction is typically carried out in an inert atmosphere, such as argon or nitrogen, at reflux for about 3 hours. The resulting compound of Formula XXI is then preferably isolated by extraction with a polar organic solvent. A preferred polar organic solvent is methylene chloride.

The thus produced compound of Formula XXI is then reacted with the an inorganic acid with heat, to yield the compound of Formula III. Exemplary inorganic acids include HCl, HBr, and HI. Preferably the reaction is heated at reflux for about 3 hours. Thereafter, the resulting crude compound of Formula III may be isolated by concentration in vacuo and the residue purified by any suitable means known to those skilled in the art. Exemplary means of purification include radial PLC and recrystallization. The reaction produces the compounds of Formula III in crystalline form.

When Y is halo in the compound of Formula III, the compound may be hydrogenated by any suitable technique, preferably by catalytic hydrogenation in the presence of a palladium catalyst in a hydrogen atmosphere under pressure (e.g., at least three atmospheres). See generally, J. March, Advanced Organic Chemistry 510–511 (3d. Ed. 1985).

As another aspect, the present invention provides a new camptothecin analog of Formula I-A:

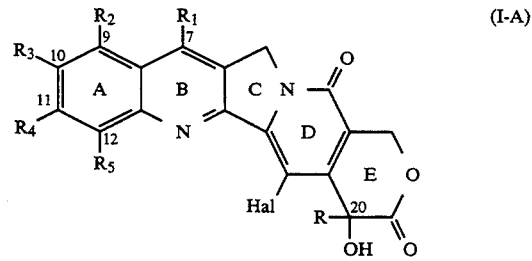

wherein:
Hal is a halogen, preferably selected from the group consisting of Cl, F, Br, or I.
R may be loweralkyl, preferably ethyl.
R$_1$ may be H, loweralkyl, loweralkoxy, or halo (e.g., chloro). Preferably R$_1$ is H.
R$_2$, R$_3$, R$_4$, and R$_5$ may each independently be H, amino, hydroxy, loweralkyl, loweralkoxy, loweralkylthio, di(loweralkyl)amino, cyano, methylenedioxy, formyl, nitro, halo, trifluoromethyl, aminomethyl, azido, amido, hydrazino, or any of the twenty standard amino acids bonded to the A ring via the amino-nitrogen atom.

At least two of R$_2$, R$_3$, R$_4$, and R$_5$ may be H, and in a preferred embodiment, R$_2$, R$_4$, and R$_5$ are H.

Preferably, R$_2$ is H or amino, R$_3$ is H or hydroxy, R$_4$ is H, and R$_5$ is H.

The compounds of Formula I-A are antineoplastic agents having antitumor and antileukemic activity. The compounds of Formula I-A are also useful for inhibiting topoisomerase enzymes in vitro and in vivo, particularly topoisomerase I. The compounds of Formula I-A are useful for inhibiting the growth of leukemia cells such as L-1210 mouse leukemia cells and human KB cancer cells in vitro and in vivo. The compounds of Formula I-A are useful for inhibiting the growth of corn and tobacco plants. The compounds of Formula I-A are also useful as a chemosterilant for the housefly, *Dendrolimus puynctatus*. Additionally, compounds of Formula I-A wherein $R_1$ is halo are useful as intermediates for among other things, making compounds of Formula I-A wherein $R_1$ is loweralkyl.

The compounds of Formula I-A above may be prepared according to Scheme E below.

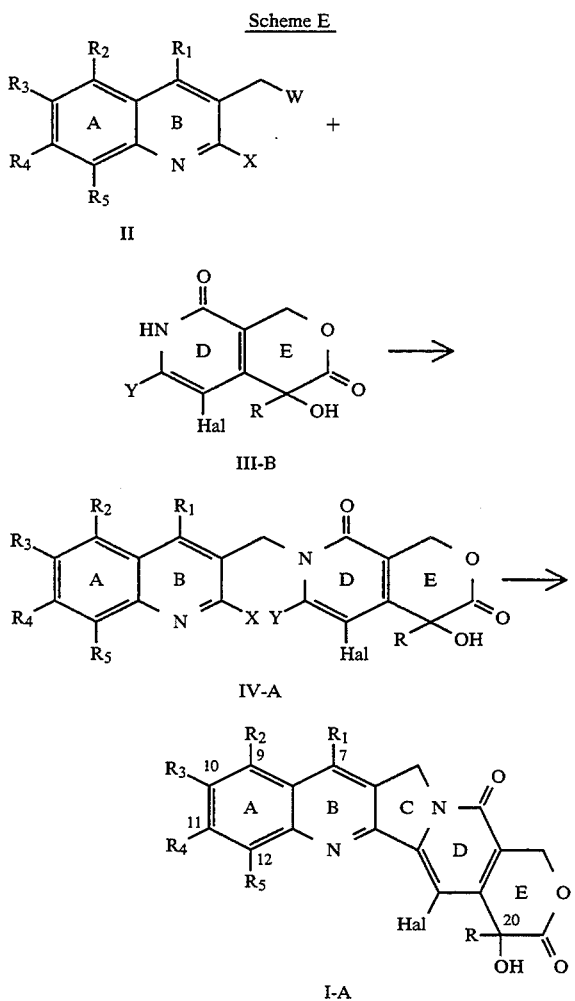

According to Scheme E above, the compounds of Formula I-A are prepared from the compounds of Formula IV-A:

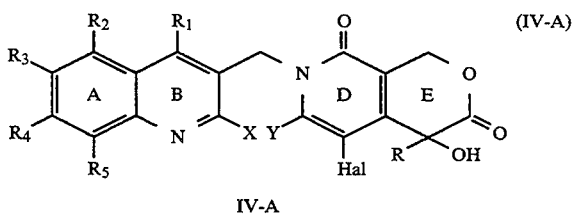

wherein Hal, R, $R_1$, $R_2$, $R_3$, $R_4$ and $R_5$ are as defined above for Formula I-A.

The compounds of Formula I-A are prepared by cyclizing the compounds of Formula IV-A by an intramolecular Heck reaction. The reaction is carried out in the presence of a palladium catalyst (e.g., palladium acetate) under basic conditions in a polar aprotic solvent such as acetonitrile or dimethylformamide. A phase transfer catalyst such as a tetraalkylammonium halide salt is preferably included. The reaction should be carried out in an inert atmosphere, such as under argon. The reaction mixture may be heated to a temperature between about 50° to about 100° C. for about 1 to 24 hours. Variations on these conditions will be apparent from the literature on the Heck reaction. See, e.g., R. Grigg et al. Tetrahedron 46,4003–4008 (1990).

As shown in Scheme E above, the compounds of Formula IV-A are prepared from the novel intermediates of Formula III-B:

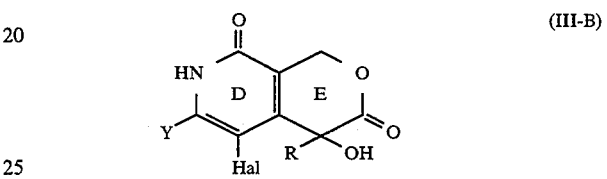

wherein:
Hal is a halogen, preferably selected from the group consisting of Cl, F, Br, and I.
R may be loweralkyl, preferrably ethyl.
Y is H or halogen, preferably H.

The intermediate of Formula III-B may be alkylated with a halomethylquinoline of Formula II in a suitable solvent, such as a polar protic solvent (e.g., isopropyl alcohol, ethanol, methanol), an aprotic solvent (e.g. 1,2-dimethoxyethane, tetrahydrofuran, toluene, acetonitrile, or dimethylformamide) or alternatively in an aqueous solution in the presence of a phase transfer catalyst. The reaction is preferably carried out under mildly basic conditions, to minimize attack on the pyridone ring oxygen. The reaction may be carried out in two stages by, first, forming the anion of the pyridone by addition of an alkali earth salt (e.g., potassium tert-butoxide) at about room temperature, and then adding the halomethylquinoline to the reaction solution and heating the solution between about 60° to about 100° C. for about 4 to 24 hours.

The compounds of Formula III-B may be prepared from the compounds of Formula III. Specifically, the compounds of Formula III-B are prepared by reacting the compounds of Formula III with a halosuccinimide. The particular halosuccinimide employed depends on the desired halo substitution of the compound of Formula IIIB. Suitable halosuccinimides include fluorosuccinimide, N-chlorosuccinimide, bromosuccinimide, and N-iodosuccinimide. Typically, the reaction is carried out in a halogenated solvent such as chloroform, dichloroethane and carbon tetrachloride. The reaction mixture may be heated to a temperature of about 60° to about 65° C. for about 5 to 75 hours, depending on the particular halo substitution sought. It will be readily apparent to one skilled in the art that the exact parameters of the halogenation reaction will depend on the particular halogen substitution desired. The exact parameters required for a particular substitution will be determinable by one skilled in the art without undue experimentation.. The isolated compounds of Formula III-B may be purified by any suitable means known to those skilled in the art. Preferrably, the compounds of Formula III-B are purified by radial PLC.

In the Examples which follow, "mg" means milligrams, "g" means grams, "M" means Molar, ml means millimeter(s), "mmol" means millimole(s), "Bu" means butyl, "BuLi" means butyllithium, "THF" means tetrahydrofuran, EtOAc means ethyl acetate, EtOH means ethanol, MeOH means methanol, "min" means minutes, "° C." means degrees Centigrade, "p.s.i." means pounds per square inch, and "PLC" means preparative thin layer chromatography.

EXAMPLE 1

Preparation of 7-Methoxycarbonyl-7-ethyl-9-hydroxy-7,9-dihydrofurano[4,5-c]-2-chloro-6-methoxy pyridine Cerium trichloride heptahydrate (10.0 g, 26.8 mmol) was placed in a dry 250-ml round-bottomed flask and heated at 145°-150° C. under vacuum (at less than 0.3 Torr) for 24 hours. Under a nitrogen atmosphere, the dry cerium trichloride powder was cooled to room temperature and resuspended in THF (70 ml). The resulting slurry was stirred vigorously under nitrogen overnight. Immediately prior to use, the cerium trichloride slurry was titrated with t-BuLi until an orange coloration was achieved.

To a solution of t-BuLi (1.7 M/pentane, 18.0 ml, 30 mmol) in 70 ml of THF at −78° C. was added 1.82 ml (11.8 mmol) of 2-bromomesitylene. After stirring at −78° C. for 1 hour, a white heterogeneous mixture resulted. To this mixture was added 2-methoxypyridine (1.13 ml, 10.7 mmol) and stirring was continued at −78° for 1 hour, at 0° C. for 1 hour, and at room temperature for 1 hour. The mixture was cooled to −78° and N-formyl-N,N',N'-trimethylethylenediamine (1.5 ml, 14 mmol) was added dropwise. After stirring at −78° C. for 1 hour, the mixture was warmed to −23° C. and n-BuLi (2.0 M/hexane, 8.0 ml, 16 mmol) was added. The mixture was stirred at −23° C. for 2 hours to give a dark solution, which was transferred via a double tipped needle to the cerium trichloride slurry in THF at −23° C. After stirring at −23° C. for 2 hour, the homogeneous solution was cooled to −78° C., and methyl α-ketobutyrate (1.83 ml, 17.1 mmol) was added in one portion. The mixture was stirred at −78° C. for 1 hour and at −23° C. for 30 min. Glacial acetic acid (3.6 ml) was added at −23° C. and stirring was continued for 10 min. After addition of 10 ml of saturated aqueous sodium bicarbonate solution, the mixture was extracted with three 70 ml portions of methylene chloride. The combined organic layers were washed with water and brine, and were dried over magnesium sulfate. The product was concentrated under reduced pressure to give 4.5 mg of crude product, which was then purified by radial PLC (methylene chloride/hexanes/EtOAc,1/1/0.1) to give 1.14 g (42%) of the lactol as a white solid. Analysis: mp 134°-135.5° C.; theory C 56.91, H 5.97, N 5.53; found C 57.18, H 6.05, N 5.26.

EXAMPLE 2

Preparation of 7-Methoxycarbonyl-7-ethyl-9-hydroxy-7,9-dihydrofurano[4,5-c]-2-chloro-6-methoxy pyridine Cerium trichloride heptahydrate (1.0 g, 2.68 mmol) was placed in a dry 25 ml round-bottomed flask and heated at 140° C. under vacuum (0.25 Torr) for 15 hours. Under a nitrogen atmosphere, the dry cerium trichloride powder was cooled to room temperature and suspended in THF (7 ml). The resulting slurry was stirred vigorously under nitrogen for 4 hours. The slurry was cooled to −78° C. and titrated with t-BuLi until an orange coloration was achieved. Meanwhile, to a solution (−78° C.) of t-BuLi (0.6 ml, 1.18 mmol) and THF (7 ml) in another 25 ml flask was added 2-chloro-6-methoxypyridine (0.133 ml, 1.07 mmol), and the mixture was stirred at −78° C. for 1 hour. N-Formyl-N,N',N'-trimethylenediamine (0.134 ml, 1.23 mmol) was added dropwise. After stirring at −78° C. for 1.5 hours, the reaction was warmed to −23° C. To the solution, was added n-BuLi (0.85 ml, 1.6 mmol), and stirring was continued for 1.5 hour at −23° C. The red solution was transferred to the cerium trichloride slurry at −23° C. via cannula and stirred for 2 hours. The reaction mixture was cooled to −78° C. and methyl α-ketobutyrate (0.23 ml, 1.7 mmol) was added quickly. The reaction was stirred at −78° C. for 1 hour and at −23° C. for 30 minutes, quenched with AcOH (0.4 ml) at −23° C., stirred for 10 minutes, and 0.7 ml of saturated sodium bicarbonate was added. The organic layer was separated and the aqueous layer was extracted with EtOAc. The combined organic extracts were washed with brine and dried over magnesium sulfate. Concentration gave the crude product which was purified by radial PLC (silica gel, 20% EtOAc/hexane) to give 52 mg (17%) pure product as a white solid. Analysis: mp 114°-115° C. (hexane); theory C 50.10, H 4.91, N 4.87; found C 50.20, H 4.92, N 4.84.

EXAMPLE 3

Preparation of 9-chloro-7-methoxypyrido [5,4-c]-2-oxo-3-ethyl-3-hydroxy-3,6-dihydropyran A mixture of the lactol of Example 1 (80 mg, 0.28 mmol) and aluminum isopropoxide (170 mg, 0.84 mmol) in isopropanol. (anhydrous, 3.5 ml) was heated at reflux for 3 hours under nitrogen. The reaction was cooled to room temperature and stirred with 3 ml of saturated potassium sodium tartarate for 1 hour. The isopropanol was evaporated in vacuo, and the residue was extracted with methylene chloride. The extract was washed with brine and dried over magnesium sulfate. Concentration gave 65 mg of crude product. Purification by radial PLC (10% EtOAc/hexane) gave 52 mg of pure product (72%). Analysis: mp 159°-160° C. (hexane); theory: C 51.27, H 4.69, N 5.44; found C 51.17, H 4.71, N 5.40; $^1$H NMR (300 MHz, CDCl$_3$) δ7.20 (s, 1 H) , 5.53 (d, 1 H, J=15.8 Hz), 5.23 (d, 1 H, J=15.8 Hz), 4.00 (s, 1 H), 1.79 (q, 2 H, J=7.4 Hz), 0.96 (t, 3 H, J=7.4 Hz); $^{13}$C NMR (300 MHz, CDCl$_3$) δ173.5, 158.3, 150.8, 148.9, 112.8, 109.8, 73.0, 65.2, 54.5, 31.7, 7.5; IR (KBr): cm$^{-1}$ 3483.5 (s), 3101.2 (s), 2962.5 (w), 1734.6 (s), 1600.4 (s), 1584.1 (s), 1460.4 (s), 1365.1 (s), 1154.5 (s), 1100.7 (s).

EXAMPLE 4

Preparation of 7-methoxypyrido [5,4-c]-2-oxo-3-ethyl-3-hydroxy-3,6-dihydropyran

A mixture of 9-chloro-7-methoxypyrido [5,4-c]-2-oxo-3-ethyl-3-hydroxy-3,6-dihydropyran (20 mg, 0.078 mmol) and sodium acetate (20 mg, 0.24 mmol) in 5 ml of EtOH was hydrogenated over 10% Pd/C (5 mg) at 42 p.s.i. for 10 hours at room temperature. The mixture was filtered through Celite and the solids were washed with MeOH. The filtrate was concentrated and the residue was purified by radial PLC (silica gel, 10% EtOAc/hexane) to give 15 mg (87%) of pure product as a white solid. Analysis: mp 107°–108° C. (hexane); $^1$H NMR (300 MHz CDCl$_3$) δ: 8.19–8.21 (d, 1 H, J=5 Hz), 7.15–7.17 (d, 1 H, J=5 Hz), 5.55–5.61 (d, 1 H, J=16 Hz), 5.24–5.29 (d, 1 H, J=16 Hz), 3.99 (s, 3 H), 3.63 (s, 1 H), 1.76–1.83 (q, 2 H, J=7 Hz), 0.93–0.98 (t, 3 H, J =7 Hz); IR (KBr): cm$^{-1}$ 3478, 3140, 1735, 1603, 1458, 1398, 1380, 1231, 1159, 1102, 1035, 845.

EXAMPLE 5

Preparation of 7-oxopyrido [5,4-c]-2-oxo-3-ethyl-3-hydroxy-3,6-dihydropyran

A mixture of the lactol of Example 1 (47 mg, 0,186 mmol) and aluminum isopropoxide (114 mg, 0,558 mmol) in isopropanol (anhydrous, 2.5 ml) was heated at reflux for 3 hours under nitrogen. The cooled reaction mixture was stirred with 2.5 ml of saturated sodium potassium tartrate at room temperature for 1 hour. The reaction mixture was diluted with 10 ml of brine and then extracted with ether. The combined ether extracts were dried over magnesium sulfate and concentrated in vacuo to give 51 mg of 7-methoxypyrido [5,4-c]-2-oxo-3-ethyl-3-hydroxy-3,6-dihydropyran as a yellow gum.

A solution of 51 mg of 7-mehoxypyrido [5,4-c]-2-oxo-3-ethyl-3-hydroxy-3,6-dihydropyran in 4 ml of 1 N HCl was heated at reflux for 3 hours. The reaction mixture was concentrated in vacuo. The residue was purified by radial PLC (silica gel, 5 % MeOH/CH$_2$Cl$_2$) to give 22 mg (57% from lactol) of 7-Oxopyrido [5,4-c]-2-oxo-3-ethyl-3-hydroxy-3,6-dihydropyran as a white solid: mp 228°–229° C.

EXAMPLE 6

Preparation of 10-chloro-7-oxopyrido [5,4-c]-2-oxo-3-ethyl-3-hydroxy-3,6-dihydropyran A suspension of 7-oxopyrido [5,4 -c]-2-oxo-3-ethyl-3-hydroxy-3,6-dihydropyran (13 mg, 0.062 mmol), N-chlorosuccinimide (8.9 mg, 0.069 mmol), and CHCl$_2$ (1 ml) was heated at reflux with vigorous stirring for 72 hours. Concentration gave the curds product which was purified by radial PLC (silica gel, 3% methanol/methylene chloride) to give 12 mg (80%) of pure product. Analysis: mp 209°–210° C. (CHCl$_3$); theory C 49.30, H 4.14, N 5.75; found C 49.13, H 4.26, N 5.65. $^1$H NMR (300 MHz, CDCl$_3$) δ: 7.49 (s, 1 H), 5.55 (d, 1 H, J=16.8 Hz), 5.13 (d, 1 H, J=16.8 Hz), 3.9 (br s, 1 H), 2.1–1.9 (m, 2 H), 1.00 (t, 3 H, J=7.4 Hz).

EXAMPLE 7

Preparation of 10-bromo-7-oxopyrido [5,4-c]-2-oxo-3-ethyl-3-hydroxy-3,6-dihydropyran A suspension of 7-oxopyrido [5,4 -c]-2-oxo-3-ethyl-3-hydroxy-3,6-dihydropyran (13 mg, 0.062 mmol), N-bromosuccinimide (12.2 mg, 0.069 mmol), and CHCl$_3$ (1 ml) was heated at reflux with vigorous stirring for 9 hours. Concentration gave the crude product which was purified by radial PLC (silica gel, 3% methanol/methylene chloride) to give 17 mg (96%) of pure product. Analysis: mp 173°–174° C. (CHCl$_3$); theory C 41.69, H 3.50, N 4.86; found C 41.48, H 3.51, N 5.83. $^1$H NMR (300 MHz, CDCl$_3$) δ: 7.66 (s, 1 H), 5.56 (d, 1 H, J=16.8 Hz), 5.13 (d, 1 H, J=16.8 Hz), 4.02 (br s, 1 H), 2.1–1.9 (m, 2 H), 1.01 (t, 3 H, J=7.5 Hz); $^{13}$C NMR (300 MHz, CDCl$_3$) δ: 172.8, 159.9, 147.0, 137.4, 121.4, 96.7, 73.3, 65.5, 31.8, 8.0.

EXAMPLE 8

Preparation of 10-iodo-7-oxopyrido [5,4-c]-2-oxo-3-ethyl-3-hydroxy-3,6-dihydropyran.

A suspension of 7-oxopyrido [5,4 -c]2 -oxo-3-ethyl-3-hydroxy-3,6-dihydropyran (13.5 mg, 0.64 mmol), N-iodosuccinimide (22 mg, 0,098 mmol), and CHCl$_3$(2 mL) was heated at refulx with vigorous stirring for 3 days. Concentration gave the crude product which was purified by radial PLC (silica gel, 3% CH$_3$OH/CH$_2$Cl$_2$) to give 20 mg (92%) of product as a yellow gum. $^1$H NMR (300 MHz, CDCl$_3$) δ: 7.83 (s, 1 H), 5.55–5.61 (d, 1 H, J =16 Hz), 5.07–5.13 (d, 1 H, J=16 Hz), 3.89 (br s, 1 H), 1.85–2.10 (m, 2 H), 0.99–1.04 (t, 3 H, J=7 Hz).

The foregoing is illustrative of the present invention and is not to be construed as limiting thereof. The invention is defined by the following claims, with equivalents of the claims to be included therein.

That which is claimed is:

1. A method for making a compound of Formula XXI:

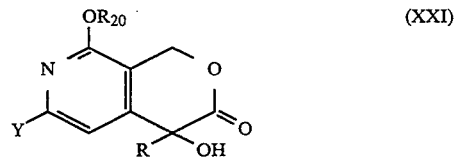

wherein R$_{20}$ is loweralkyl, R is loweralkyl and Y is H or halogen; by reacting a compound of Formula XX:

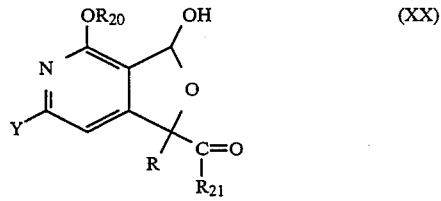

wherein R$_{21}$ is lower alkoxy; with a reducing agent in a polar solvent with heat, to yield the compound of Formula XXI.

2. The method according to claim 1, wherein said compound of Formula XX is prepared by:
   (a) combining a pyridine compound selected from the group consisting of 2-methoxypyridine and 5-chloro-2-methoxypyridine, with mesityllithium to form a reaction mixture;
   (b) reacting the mixture produced in step (a) with a formamide of an ethylenediamine;
   (c) reacting the mixture of step (b) with a base of the Formula A$^+$B$^-$, wherein A$^+$ is an inorganic cation, and B$^-$ is an organic anion, to produce an intermediate;
   (d) reacting the intermediate of step (c) with anhydrous cerium trichloride to form a reaction product; and
   (e) reacting the product of step (d) with an alkyl α-ketobutyrate; to produce the compound of Formula XX.

3. The method according to claim 1, wherein the reducing agent is aluminum isopropoxide.

4. The method according to claim 2, wherein the formamide of an ethylenediamine is N-formyl-N,N',N'-trimethylethylenediamine.

5. The method according to claim 2, wherein the inorganic cation $A^+$ is selected from the group consisting of sodium, potassium, and lithium.

6. The method according to claim 2, wherein said organic anion $B^-$ is selected from the group consisting of propyl, n-butyl, phenyl, and n-pentyl.

7. The method according to claim 2, wherein the alkyl α-ketobutyrate is methyl α-ketobutyrate.

8. The method according to claim 1, wherein $R_{20}$ is methyl.

9. The method according to claim 1, wherein $R_{21}$ is methoxy.

10. The method according to claim 1, wherein R is ethyl.

11. The method according to claim 1, wherein Y is H.

12. A method of making a compound of Formula XX:

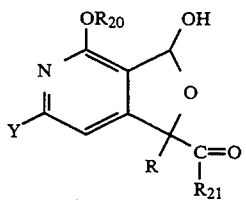

wherein $R_{20}$ is loweralkyl, $R_{21}$ is lower alkoxy,
R is loweralkyl, and Y is H or halogen; said method comprising:
(a) reacting a pyridine compound selected from the group consisting of 2-methoxypyridine and 5-chloro-2methoxypyridine, with mesityllithium to form a reaction mixture;
(b) reacting the mixture of step (a) with a formamide of ethylenediamine;
(c) reacting the mixture of step (b) with a base of the Formula $A^+B^-$, wherein $A^+$ is an inorganic cation, and $B^-$ is an organic anion to produce an intermediate;
(d) reacting the intermediate of step (c) with anhydrous cerium trichloride; and
(e) reacting the product of step (d) with an alkyl α-ketobutyrate; to produce the compound of Formula XX.

13. The method according to claim 12, wherein the formamide of an ethylenediamine is N-formyl-N,N',N'-trimethylethylenediamine.

14. The method according to claim 12, wherein the inorganic cation $A^+$ is selected from the group consisting of sodium, potassium, and lithium.

15. The method according to claim 12, wherein said organic anion $B^-$ is selected from the group consisting of propyl, n-butyl, phenyl, and n-pentyl.

16. The method according to claim 12, wherein the alkyl α-ketobutyrate is methyl α-ketobutyrate.

17. The method according to claim 12, wherein $R_{20}$ is methyl.

18. The method according to claim 12, wherein $R_{21}$ is methoxy.

19. The method according to claim 12, wherein R is ethyl.

20. The method according to claim 12, wherein Y is H.

21. A compound of Formula XX:

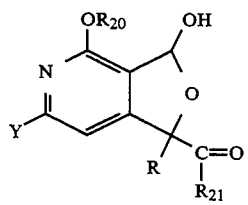

wherein $R_{20}$ is loweralkyl, $R_{21}$ is lower alkoxy,
R is loweralkyl, and Y is H or halogen.

22. The compound according to claim 21, wherein $R_{20}$ is methyl.

23. The compound according to claim 21, wherein $R_{21}$ is methoxy.

24. The compound according to claim 21, wherein R is ethyl.

25. The compound according to claim 21, wherein Y is H.

26. The compound according to claim 21, wherein Y is halogen.

* * * * *